United States Patent [19]

Brunelle

[11] 4,353,793

[45] Oct. 12, 1982

[54] METHOD FOR REMOVING POLYHALOGENATED HYDROCARBONS FROM NONPOLAR ORGANIC SOLVENT SOLUTIONS

[75] Inventor: Daniel J. Brunelle, Scotia, N.Y.

[73] Assignee: General Electric Company, Schenectady, N.Y.

[21] Appl. No.: 305,760

[22] Filed: Sep. 25, 1981

[51] Int. Cl.³ ........................ C07C 7/10; C10G 19/02; C10G 21/16

[52] U.S. Cl. ........................ 208/262; 585/864

[58] Field of Search ................ 208/262; 585/864, 868; 570/240

[56] References Cited

U.S. PATENT DOCUMENTS

| | | | |
|---|---|---|---|
| 2,160,632 | 5/1939 | Yabroff et al. | 585/864 |
| 2,183,801 | 12/1939 | Yabroff | 585/864 |
| 2,212,105 | 8/1940 | Yabroff | 585/864 |

FOREIGN PATENT DOCUMENTS

| | | | |
|---|---|---|---|
| 564683 | 10/1958 | Canada | 208/262 |

OTHER PUBLICATIONS

O. Hutzinger et al., "Reaction with Alkoxide", Chemistry of PCB's, pp. 115–118.

Leo Weitzman, "Treatment and Destruction of PCB and PCB Contaminated Materials", Preprint Extended Abstract, Presented before the Division of Environmental Chemistry, Am. Chem. Soc., NY, NY, Aug. 1981, pp. 42–44.

Pytlewski et al., "The Reaction of PCB's with Sodium Oxygen, and Polyethylene Glycols", U.S. EPA Off. Research and Development, Treatment of Hazardous Waste Symposium, (1980), pp. 72–76.

Franklyn Institute, U.S. patent application Ser. No. 158,359, Filed Nov. 6, 1980, Derwent Abstract Service, Access No. 79972 D/44.

*Primary Examiner*—Curtis R. Davis
*Assistant Examiner*—Helane E. Maull
*Attorney, Agent, or Firm*—William A. Teoli; James C. Davis, Jr.

[57] ABSTRACT

A method is provided for reducing the level of polychlorinated aromatic hydrocarbons, "PCB's", while dissolved in an organic solvent, for example, transformer oil. Removal of the polychlorinated aromatic hydrocarbon, can be accomplished by treating the contaminated solution with a mixture of monocapped polyalkyleneglycol alkyl ether and an alkali metal hydroxide.

6 Claims, No Drawings

METHOD FOR REMOVING POLYHALOGENATED HYDROCARBONS FROM NONPOLAR ORGANIC SOLVENT SOLUTIONS

CROSS REFERENCE TO RELATED APPLICATIONS

Reference is made to my copending application Ser. No. 269,121, filed June 1, 1981, for "Method for Removing Polyhalogenated Hydrocarbons From Nonpolar Organic Solvent Solutions" and copending application of John M. Brown, Jr. et al, Ser. No. 212,387, for "Method for Removing Polychlorinated Biphenyls from Transformer Oil", filed Dec. 3, 1980 where the aforementioned applications are assigned to the same assignee as the present invention.

BACKGROUND OF THE INVENTION

Polychlorinated biphenyls, or "PCB's" were long used as dielectric fluids in electrical equipment because these materials have excellent heat stability, are nonflammable in nature, have low volatility and a good viscosity characteristic at operation temperatures. Because of their environmental persistence, however, continued manufacture, import, or use in the United States was banned under the Toxic Substances control Act of 1976, and the U.S. Environmental Protection Agency was directed to promulgate rules and regulations for their removal from the economy.

As of July 1, 1979, EPA regulations defined as "PCB-contaminated" any material containing more than 50 ppm of a mono-, di-, or polychlorinated biphenyl. The regulations permit disposal of PCB-contaminated materials by either incineration in an approved manner or in an approved landfill, but such procedures have rarely proven acceptable to community neighbors. Since considerable fractions of the transformer oils, e.g., refined asphaltic-base mineral oil, or heat exchange oils, e.g., hydrogenated terphenyls, now in service are PCB-contaminated, the problem of disposing of PCB-contaminated hydrocarbon oils in an effective manner presents a serious challenge. As used hereinafter, the term "transformer oil" signifies a mineral insulating oil of petroleum origin for use as an insulating and cooling media in electrical apparatus, for example, transformers, capacitors, underground cables, etc.

Various techniques for meeting this challenge have been proposed. One method is shown by D. K. Parker et al, Plant engineering, Aug. 21, 1980, Pages 133–134. The method of Parker et al is based on the formation of a solution of an organo-sodium reagent, such as sodium naphthalenide, in a carrier solvent, for example, tetrahydrofuran, which is then added to the contaminated oil. The Parker et al process requires a multistep procedure involving first the formation of organo-sodium reagent, next the incorporation of such organo-sodium compound into the PCB-contaminated oil followed by at least 2 more hours for the reaction to be complete, followed by a water quench and distillation and purification steps to recycle the tetrahydrofuran. Another procedure, somewhat similar to the Parker et al process, is described by Smith et al, University of Waterloo, based on the graduate thesis of James G. Smith and G. L. Bubbar, "The Chemical Destruction of Polychlorinated Biphenyls by Sodium Naphthalenide". Again, a lengthy, multistep procedure is necessary before effective destruction of the PCB is achieved. A further procedure is shown by Hiraoka e al, Japan Kokai 74,822,570, Chem. Abstracts 8988831K, Vol. 82, 1975, which describes the destruction of polychlorinated biphenyls utilizing a sodium dispersion in Kerosene, but requires a 6 hour heating period at 120° C.

Recently, Lewis L. Pytlewski et al, demonstrated that PCB's, as well as representative halogenated pesticides were found to be rapidly and completely decomposed by the use of molten sodium metal dispersed in polyethyleneglycol. The Pytlewski et al technique is shown in the reaction of PCB's with sodium, oxygen, and polyethyleneglycols, Chemistry and Biosciences Lab, Franklyn Research Center, Philadelphia, Pa. 19103. However, the use of metallic sodium metal requires the special handling and trace amounts of water must be eliminated to minimize dangerous side reactions.

In my copending application Ser. No. 269,121, filed June 1, 1981, I found that PCB's could be destroyed or effectively removed from transformer oil, or other inert organic solvents, by reaction of the PCB contaminated solvent with a polyoxyalkyleneglycol and alkali metal hydroxide at a temperature up to about 200° C.

The present invention is based on my discovery that substantially improved results can be achieved with respect to rate of PCB removal from contaminated organic solvents by using mono-capped polyalkyleneglycol, $C_{(1\text{-}4)}$ alkyl ethers, for example, monocapped polyethyleneglycol methylethers (PEGM) with alkali metal hydroxides, for example, potassium hydroxide. I have found that a 3–5 fold increase in reaction rate results for either completely eliminating, or substantially reducing polyhalogenated aromatic hydrocarbon in substantially inert organic solvents by the practice of the present invention as compared to the method described in Ser. No. 269,121.

STATEMENT OF THE INVENTION

There is provided by the present invention a method of treating a PCB contaminated solution of a substantially inert organic solvent having a concentration of polyhalogenated aromatic hydrocarbon at up to 1% by weight to reduce the polyhalogenated aromatic hydrocarbon concentration to less than 50 ppm, which comprises, agitating a mixture at a temperature of 25° C. to 200° C. comprising such substantially inert organic solvent solution of polyhalogenated aromatic hydrocarbon, monocapped polyalkyleneglycol alkyl ether and alkali metal hydroxide for a time which is at least sufficient to effect the minimum aforedescribed reduction in concentration of the polyhalogenated aromatic hydrocarbon in the agitated mixture, which comprises by weight, (A) up to 1% of polyhalogenated aromatic hydrocarbon, (B) about 0.1 to 10% of monocapped polyalkyleneglycol alkyl ether, (C) about 0.1 to 10% of alkali metal hydroxide, and (D) about 80 to 99.8% of substantially inert organic solvent, where the sum of (A)+(B)+(C)+(D) is equal to 100%.

Monocapped polyalkyleneglycol alkyl ethers which can be used in the practice of the present invention are, for example, polymers having a molecular weight in the range of from about 200 to 5000 and include, for example, polyethyleneglycol monoethyl ethers having molecular weights in the range of 350–750, manufactured by the Aldrich Chemical Company of Milwaukee, Wis.

Alkali metal hydroxides which can be used in the practice of the present invention are, for example, sodium hydroxide, potassium hydroxide, cesium hydroxide, etc.

In the practice of the present invention, a mixture of monocapped polyalkyleneglycol alkyl ether (PEGM) and alkali metal hydroxide is utilized in combination with PCB contaminated nonpolar organic solvent. The resulting mixture is thereafter agitated in an oxidizing or non-oxidizing atmosphere until the level of the PCB contaminant is reduced to less than 50 ppm of polyhalogenated aromatic hydrocarbon.

Temperatures in the range of between 90° C. to 120° C. is preferred, whereas a temperature in the range of between 25° C. to 200° C. can be used.

It has been found that a proportion of 1 to 50 equivalents of alkali metal of the alkali metal hydroxide, per OH of the monocapped polyalkyleneglycol can be used to make the M'OH/PEGM reagent, where M' represents an alkali metal as previously defined with respect to the alkali metal hydroxide usage, while PEGM represents monocapped polyalkyleneglycol alkyl ether and preferably monocapped polyethyleneglycol methyl ether as previously defined.

It has been found that effective results can be achieved if at least one equivalent of alkali metal, per OH of the PEGM will be effective for removing one equivalent of halogen atom from the PCB. Higher amounts are preferably used to facilitate PCB removal.

The M'OH/PEGM reagent, can be preformed, or the aforementioned ingredients can be added separately within the aforementioned limits to the PCB contaminated, nonpolar organic solvent. Experience has shown that agitation of the resulting mixture, such as stirring or shaking, is necessary to achieve effective results when the M'OH/PEGM reagent has been introduced into the contaminated nonpolar organic solvent.

In order to effectively monitor the reduction or removal of PCB or polyhalogenated aromatic hydrocarbon contamination, such as polychlorinated biphenyl contamination in the non-polar or substantially inert organic solvent, a vapor phase chromatograph, for example, Model No. 3700, of the Varian Instrument Company, can be used in accordance with the following procedure:

An internal standard, for example, n-docosane can be added to the initial reaction mixture. The standard is then integrated relative to the PCB envelope to determine ppm concentration upon VPC analysis.

In order that those skilled in the art will be better able to practice the invention, the following examples are given by way of illustration and not by way of limitation. All parts are by weight.

EXAMPLE 1

Heterogenous mixtures of polyethyleneglycol methylether, 85% KOH pellets, heptane and a standard solution of Arochlor 1260 in N-docosane were magnetically stirred and heated to 75° C. Aliquots of the mixtures were periodically removed and analyzed by VPC on an OV-17 column and 150°–250° C., and integration relative to the internal standard showed the amount of Arochlor remaining. Several runs were made with polyethyleneglycol methylether at various molecular weights, Triton X-100, an isooctylphenoxypolyethoxyethanol having an average of 10 moles of ethyleneoxide units, and manufactured by the Rohm and Haas Company, as a surfactant was also included. The reaction time employed for the various runs was ½ hour to 2 hours. In certain instances, reactions were conducted under an oxygen atmosphere and an inert atmosphere (nitrogen). In one instance, the mixture was not stirred. All mixtures were run relative to the parts shown in Table I with 48 parts of heptane and 2.7 parts of a standard solution of Arochlor 1260 in N-dodosane containing 1.00 part of Arochlor 1260. The following results were obtained, where "PEG" is polyethyleneglycol, "PEGMA" is monocapped polyethyleneglycol methylether "% Arochlor Consumed" is the amount of residue compared to the original amount of Arochlor as shown by VPC analysis on an OV-17 column at 150°–250° C. and integrated relative to an internal standard:

TABLE I

| PEG or PEGM (parts) | Base (parts) | Time (hr) | Arochlor % Consumed |
|---|---|---|---|
| PEG 600 (6.67) | KOH (2.75) | 1 | 21 |
| | | 2 | 82 |
| PEGM 550 (6.11) | KOH (2.76) | 1 | 61 |
| | | 2 | 88 |
| PEGM 750 (8.33) | KOH (2.75) | 1 | 81 |
| | | 2 | 93 |
| Triton X-100 (3.31) | KOH (1.46) | 1 | 78 |
| | | 2 | 84 |
| PEG 600 (2.83) | KOH (4.58) | ½ | 12 |
| | | 1 | 19 |
| PEG 1000 (3.33) | KOH (4.58) | ½ | 33 |
| | | 1 | 50 |
| PEG 3400 (9.35) | KOH (4.58) | ½ | 58 |
| | | 1 | 60 |
| PEGM 750 (4.17) | KOH (3.66) | ½ | 72 |
| | | 1 | 78 |
| PEGM 1900 (8.97) | KOH (2.93) | ½ | 75 |
| | | 1 | 85 |
| PEGM 750 (4.167) | NaOH (2.56) | ½ | 30 |
| | | 1 | 40 |
| PEGM 750 (4.17) | 50% NaOH (5.11) | ½ | 12 |
| | | 1 | 16 |
| PEGM 750 (4.17) | $Na_2O$ (3.96) | ½ | 35 |
| | | 1 | 54 |
| PEGM 750 (4.17) | KOH (3.66) | ½ | 69 |
| | | 1 | 78 |
| PEGM 750 (4.17) | KOH (3.66) | ½ | 62 |
| | | 1 | 74 |
| PEGM 750 (4.17) | KOH (3.66) | ½ | 5 |
| | | 1 (NS)* | |

*No Stirring

The above table indicates that monocapped polyethyleneglycol methyl ether reacts three to five times faster than polyethyleneglycol with Arochlor 550 after ½ hour or 1 hour if a comparison is made between PEG 600 and PEGM 550 and PEG 600 and PEGM 750. It also appears that an increase in molecular weight increases she effectiveness of the PEG or PEGM. However more of the polyalkyleneglycol was required. In addition Triton X also indicates that monocapped-polyalkyleneglycols containing aryl substitution also can be used in the practice of the invention. However, these aryl-substituted monocapped polyalkyleneglycol ethers can result in emulsification which may not be desirable in certain situations.

EXAMPLE 2

There was added to 100 parts of transformer oil containing approximately 600 ppm of PCB, 3–5% by weight of a polyethyleneglycol or monocapped polyethyleneglycol methylether (PEGM) along with a 3–6% by weight of 85% KOH. The heterogeneous mixtures were stirred at a temperature of between 60° C. to 130° C. for 1 hour. The resulting brown-black mixture was cooled and filtered through Celite and was submitted for VPC analysis. The VPC analysis was done with an electron capture detector to determine the remaining PCB's, if any, in the mixture. The following results were obtained:

TABLE II

| PEG (WT %) | KOH (WT %) | ppm PCB remaining |
|---|---|---|
| PEGM 750 (3%) | 3 | 60 |
| PEGM 750 (4%) | 4 | 17 |
| PEGM 750 (5%) | 5 | 6 |
| PEGM 550 (4%) | 4 | 9 |
| PEG 400 (4%) | 6 | 115 |
| PEG 600 (4%) | 4.5 | 108 |
| PEGM 350 (4%) | 6 | 0[b] |
| PEGM 550 (4%) | 6 | 0[b] |

[b]Reaction at 110° C.

The above results show that the most effective PEGM for PCB removal is PEGM 350 or 550.

Although the above examples are directed to only a few of the very many variables which can be employed in the practice of the present invention, it should be understood that the present invention is directed to the use of a much broader variety of monocapped-polyalkyleneglycol $C_{(1-4)}$ ethers, as well as aryl-substituted monocapped polyalkyleneglycol ethers with alkali metal hydroxides to effect PCB removal or consumption in contamonated organic solvents.

What I claim as new and desired to secure by Letters Patent of the United States is:

1. A method of treating a PCB contaminated solution of a substantially inert organic solvent having a concentration of polyhalogenated aromatic hydrocarbon at up to 1% by weight to reduce the polyhalogenated aromatic hydrocarbon concentration to less than 50 ppm, which comprises, agitating a mixture at a temperature of 25° C. to 200° C. comprising such substantially inert organic solvent solution of polyhalogenated aromatic hydrocarbon, monocapped-polyalkyleneglycol alkyl ether and alkali metal hydroxide for a time which is at least sufficient to effect the minimum aforedescribed reduction in concentration of the polyhalogenated aromatic hydrocarbon in the agitated mixture which comprises by weight, (A) up to 1% of polyhalogenated aromatic hydrocarbon, (B) about 0.1 to 10% of monocapped-polyalkyleneglycol alkyl ether, (C) about 0.1 to 10% of alkali metal hydroxide, and (D) about 80 to 99.8% of substantially inert organic solvent, where the sum of (A)+(B)+(C)+(D) is equal to 100%.

2. A method in accordance with claim 1, where the monocapped polyalkyleneglycol alkyl ether is a polyethyleneglycol having a molecular weight of about 400.

3. A method in accordance with claim 1, where the monocapped polyalkyleneglycol alkyl ether is monocapped-polyethylene glycol methyl ether.

4. A method in accordance with claim 1, where the alkali metal hydroxide is potassium hydroxide.

5. A method in accordance with claim 1, where the sustantially inert organic solvent is transformer oil.

6. A method in accordance with claim 1, where the polyhalogenated aromatic hydrocarbon is a polychlorinated biphenyl.

* * * * *